US010634637B2

(12) United States Patent
Potyrailo et al.

(10) Patent No.: US 10,634,637 B2
(45) Date of Patent: Apr. 28, 2020

(54) HIGHLY SELECTIVE CHEMICAL AND BIOLOGICAL SENSORS

(71) Applicant: General Electric Company, Schenectady, NY (US)

(72) Inventors: Radislav Alexandrovich Potyrailo, Niskayuna, NY (US); Cheryl Margaret Surman, Albany, NY (US); Binil Kandapallil, Mechanicville, NY (US)

(73) Assignee: General Electric Company, Schenectady, NY (US)

( * ) Notice: Subject to any disclaimer, the term of this patent is extended or adjusted under 35 U.S.C. 154(b) by 187 days.

(21) Appl. No.: 15/794,815

(22) Filed: Oct. 26, 2017

(65) Prior Publication Data

US 2018/0045671 A1 Feb. 15, 2018

Related U.S. Application Data

(62) Division of application No. 12/977,568, filed on Dec. 23, 2010, now abandoned.

(51) Int. Cl.
*G01N 27/327* (2006.01)
*G01N 33/487* (2006.01)
*G01N 27/02* (2006.01)

(52) U.S. Cl.
CPC ....... *G01N 27/3278* (2013.01); *G01N 27/025* (2013.01); *G01N 33/48792* (2013.01)

(58) Field of Classification Search
CPC .............. G01N 27/3278; G01N 27/025; G01N 33/48792
See application file for complete search history.

(56) References Cited

U.S. PATENT DOCUMENTS

2007/0090926 A1 4/2007 Potyrailo et al.
2009/0278685 A1 11/2009 Potyrailo et al.

OTHER PUBLICATIONS

Lindholm-Sethson, Britta, et al. "Electrochemical impedance spectroscopy in label-free biosensor applications: multivariate data analysis for an objective interpretation." Analytical and bioanalytical chemistry 398.6 (2010): 2341-2349.*

(Continued)

*Primary Examiner* — Robert J Eom
(74) *Attorney, Agent, or Firm* — Jean K. Testa; Fletcher Yoder, P.C.

(57) ABSTRACT

Methods and sensors for selective fluid sensing are provided. A sensor includes a resonant inductor-capacitor-resistor (LCR) circuit and a sensing material disposed over the LCR circuit. The sensing material includes a coordination compound of a ligand and a metal nanoparticle. The coordination compound has the formula: $(X)_n$-M, where X includes an alkylamine group having the formula (R—$NH_2$), an alkylphosphine having the formula ($R_3$—P), an alkylphosphine oxide having the formula ($R_3P$=O), an alkyldithiocarbamate having the formula ($R_2NCS_2$), an alkylxanthate having the formula ($ROCS_2$), or any combination thereof, R includes an alkyl group, n is 1, 2, or 3, and M includes the metal nanoparticle of gold, silver, platinum, palladium, alloys thereof, highly conductive metal nanoparticles, or any combination thereof. The sensing material is configured to allow selective detection of at least six different analyte fluids from an analyzed fluid mixture.

11 Claims, 4 Drawing Sheets

(56) References Cited

OTHER PUBLICATIONS

Potyrailo, R., et al.; Development of Radio-Frequency Identification Sensors Based on Organic Electronic Sensing Materials for Selective Detection of Toxic Vapors; American Institute of Physics, Journal of Applied Physics 106, 124902 (2009), pp. 124902-1 through 124902-6 (6 pages).
Potyrailo, R., et al.; Selective Quantitation of Vapors and their Mixtures using Individual Passive Multivariable RFID Sensors; IEEE RFD; 2010; pp. 22-28 (7 pages).
Potyrailo, R., et al.; RFID Sensors based on Ubiquitous Passive 13.56-MHz RFID Tags and Complex Impedance Detection; 2008 John Wiley & Sons, Ltd. (13 pages).
Tan, E., et al.; A Wireless, Passive Sensor for Quantifying Packaged Food Quality; Sensors ISSN 1424-8220; Sep. 5, 2007; 7, 1747-1756 (10 pages).
Kumar, A., et al.; Investigation into the Interaction between Surface-Bound Alkylamines and Gold Nanoparticles; 2003 American Chemical Society; Langmuir, vol. 19; 6277-6282 (6 pages).
Leff, D., et al.; Synthesis and Characterization of Hydrophobic, Organically-Soluble Gold Nanocrystals Functionalized with Primary Amines; 1996 American Chemical Society; Langmuir, vol. 12; 4723-4730 (8 pages).
Briglin et al., Detection of organic mercaptan vapors using thin films of alkylamine-passivated gold nanocrystals, Langmuir 2004, 20, p. 299-305.
Westafer et al., Functionalization of high frequency SAW RFID devices for ozone dosimetry, IEEE Sensors, Oct. 25-28, 2009, p. 1747-1752.
Grate et al., Sorptive behavior of monolayer-protected gold nanoparticle films: implications for chemical vapor sensing, Anal. Chem. 2003, 75, p. 1868-1879.

\* cited by examiner

US 10,634,637 B2

HIGHLY SELECTIVE CHEMICAL AND BIOLOGICAL SENSORS

CROSS-REFERENCE TO RELATED APPLICATION

This application is a divisional of U.S. application Ser. No. 12/977,568 entitled "Highly Selective Chemical and Biological Sensors," filed Dec. 23, 2010, which is hereby incorporated by reference in its entirety.

STATEMENT REGARDING FEDERALLY SPONSORED RESEARCH & DEVELOPMENT

This invention was made with Government support and funded in part by the National Institute of Environmental Health Sciences under Grant No. 1R01ES016569-01A1. The Government has certain rights in the invention.

BACKGROUND

The subject matter disclosed herein relates to chemical and biological sensors, and more particularly, to highly selective chemical and biological sensors.

Chemical and biological sensors are often employed in a number of applications where the detection of various vapors may be used to discern useful information. For instance, measuring the presence of vapors by discerning a change in certain environmental variables within or surrounding a sensor may be particularly useful in monitoring changes in biopharmaceutical products, food or beverages, monitoring industrial areas for chemical or physical hazards, as well as in security applications, such as residential home monitoring, home land security in airports, in different environmental and clinical settings, and other public venues wherein detection of certain harmful and/or toxic vapors may be particularly useful.

One technique for sensing such environmental changes is by employing a sensor, such as an RFID sensor, coated with a particular sensing material. In addition, sensors may be arranged in an array of individual transducers, which are coated with one or more sensing materials. Many sensor arrays include a number of identical sensors. However, while using identical sensors simplifies fabrication of the sensor array, such an array may have limited capabilities for sensing only a single response (e.g. resistance, current, capacitance, work function, mass, optical thickness, light intensity, etc). In certain applications multiple responses or changes in multiple properties may occur. In such applications, it may be beneficial to include an array of sensors wherein different transducers in the array employ the same or different responses (e.g. resistance, current, capacitance, work function, mass, optical thickness, light intensity, etc.) and are coated with different sensing materials such that more than one property can be measured. Disadvantageously, fabricating a sensor array having individual sensors uniquely fabricated to sense a particular response, complicates fabrication of the array.

Further, in many practical applications, it is beneficial to use highly selective chemical and biological sensors. That is, it is often desirable to provide a sensor array capable of sensing multiple vapors and vapor mixtures in the presence of other vapors and mixtures. The greater the number of vapors and vapor mixtures that may be present, the more difficult it may be to accurately sense and discern a specific type of vapor or vapor mixture being sensed. This may be particularly true when one or more vapors are present at levels of magnitude greater than the other vapors of interest for detection. For instance, high humidity environments often interfere with the ability of traditional sensors to detect selected vapors.

Various embodiments disclosed herein may address one or more of the challenges set forth above.

BRIEF DESCRIPTION

In accordance with one embodiment, there is provided a sensor that includes a resonant inductor-capacitor-resistor (LCR) circuit and a sensing material disposed over the LCR circuit. The sensing material includes a coordination compound of a ligand and a metal nanoparticle. The coordination compound has the formula: $(X)_n$-M, where X includes an alkylamine group having the formula (R—$NH_2$), an alkylphosphine having the formula ($R_3$—P), an alkylphosphine oxide having the formula ($R_3$P=O), an alkyldithiocarbamate having the formula ($R_2NCS_2$), an alkylxanthate having the formula ($ROCS_2$), or any combination thereof, R includes an alkyl group, n is 1, 2, or 3, and M includes the metal nanoparticle of gold, silver, platinum, palladium, alloys thereof, highly conductive metal nanoparticles, or any combination thereof. The sensing material is configured to allow selective detection of at least six different analyte fluids from an analyzed fluid mixture.

In accordance with another embodiment, there is provided a method of detecting chemical or biological species in a fluid. The method includes measuring a real part and an imaginary part of an impedance spectrum of a resonant sensor antenna coated with a coordination compound of a ligand and a metal nanoparticle. The ligand includes a primary alkyl amine, trialkylphosphine, trialkylphosphine oxide, alkyldithiocarbamate, alkylxanthate or any combination thereof. The method further includes calculating at least six spectral parameters of the resonant sensor antenna coated with the coordination compound. The method further includes reducing the impedance spectrum to a single data point using multivariate analysis to selectively identify an analyte. The method further includes determining one or more environmental parameters from the impedance spectrum.

In accordance with another embodiment, there is provided a sensor that includes a transducer and a coordination compound of a ligand and a metal nanoparticle disposed on the transducer. The transducer has a multivariate output to independently detect effects of different environmental parameters on the sensor. The coordination compound has a preserved magnitude of response to an analyte over a broad concentration range of an interferent. In addition, the coordination compound has the formula: $(X)_n$-M, where X includes an alkylamine group having the formula (R—$NH_2$), an alkylphosphine having the formula ($R_3$—P), an alkylphosphine oxide having the formula ($R_3$P=O), an alkyldithiocarbamate having the formula ($R_2NCS_2$), an alkylxanthate having the formula ($ROCS_2$), or any combination thereof, R includes an alkyl group, n is 1, 2, or 3, and M includes the metal nanoparticle of gold, silver, platinum, palladium, alloys thereof, highly conductive metal nanoparticles, or any combination thereof.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
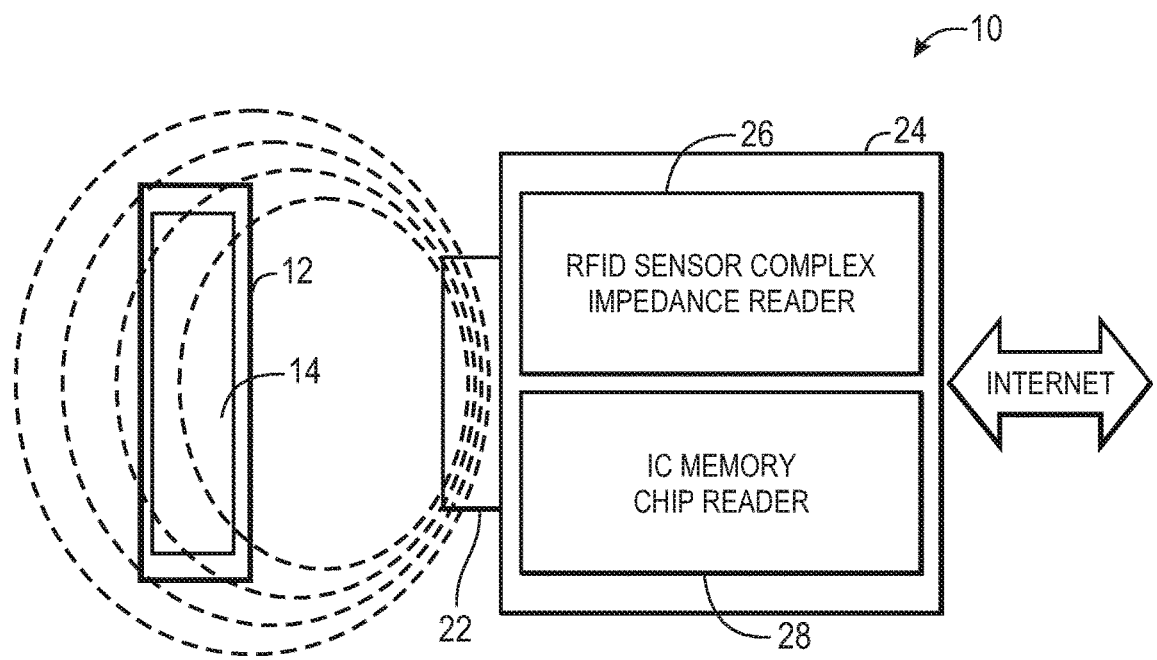
FIG. 1 illustrates a sensing system, in accordance with embodiments of the invention.

Embodiments disclosed herein provide methods and systems for selective vapor sensing wherein a single sensor is provided and is capable of detecting multiple vapors and/or mixtures of vapors alone, or in the presence of one another. Examples of such methods and sensors are described in U.S. patent application Ser. No. 12/942,732 entitled "Highly Selective Chemical and Biological Sensors," which is incorporated herein by reference. The disclosed sensors are capable of detecting different vapors and mixtures even in a high humidity environment or an environment wherein one or more vapors has a substantially higher concentration (e.g. 10×) compared to other components in the mixture. Each sensor includes a resonant inductor-capacitor-resistor (LCR) sensor that is coated with a sensing material, namely a coordination compound of a primary alkyl amine and a metal nanoparticle, as further described below. Sensing materials that include exemplary coordination compounds may provide improved ability for selective vapor sensing and improved stability of response compared to the performance of other sensing materials, such as sensing materials that include thiol groups. Non-limiting examples of LCR sensors include RFID sensors with an integrated circuit (IC) memory chip, RFID sensors with an IC chip, and RFID sensors without an IC memory chip (chipless RFID sensors). LCR sensors can be wireless or wired. In order to collect data, an impedance spectrum is acquired over a relatively narrow frequency range, such as the resonant frequency range of the LCR circuit. The technique further includes calculating the multivariate signature from the acquired spectrum and manipulating the data to discern the presence of certain vapors and/or vapor mixtures. The presence of vapors is detected by measuring the changes in dielectric, dimensional, charge transfer, and other changes in the properties of the materials employed by observing the changes in the resonant electronic properties of the circuit. By using a mathematical procedure, such as principal component analysis (PCA) and others, multiple vapors and mixtures can be detected in the presence of one another and in the presence of an interferent as further described below. Embodiments disclosed herein provide methods and systems for selective fluid sensing wherein a single sensor is provided and is capable of detecting multiple fluids and/or mixtures of fluids alone, or in the presence of one another.

To more clearly and concisely describe the subject matter of the claimed invention, the following definitions are provided for specific terms, which are used in the following description and the appended claims.

The term "fluids" includes gases, vapors, liquids, and solids.

The term "digital ID" includes all data stored in a memory chip of the RFID sensor. Non-limiting examples of this data are manufacturer identification, electronic pedigree data, user data, and calibration data for the sensor.

The term "monitoring process" includes, but is not limited to, measuring physical changes that occur around the sensor. For example, monitoring processes including monitoring changes in a biopharmaceutical, food or beverage manufacturing process related to changes in physical, chemical, and/or biological properties of an environment around the sensor. Monitoring processes may also include those industry processes that monitor physical changes as well as changes in a component's composition or position. Non-limiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor upon a change in the measured environmental parameter (temperature, pressure, chemical concentration, biological concentration, etc.). Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of sensing material and transducer geometry to enhance the selectivity of the sensor in dynamic and steady state measurements of individual vapors and their mixtures.

The term "environmental parameters" is used to refer to measurable environmental variables within or surrounding a manufacturing or monitoring system. The measurable environmental variables comprise at least one of physical, chemical, and biological properties and include, but are not limited to, measurement of temperature, pressure, material concentration, conductivity, dielectric property, number of dielectric, metallic, chemical, or biological particles in the proximity or in contact with the sensor, dose of ionizing radiation, and light intensity.

The term "analyte" includes any desired measured environmental parameter.

The term "interference" includes any undesired environmental parameter that undesirably affects the accuracy and precision of measurements with the sensor. The term "interferent" refers to a fluid or an environmental parameter (that includes, but is not limited to temperature, pressure, light, etc.) that potentially may produce an interference response by the sensor.

The term "multivariate analysis" refers to a mathematical procedure that is used to analyze more than one variable from the sensor response and to provide the information about the type of at least one environmental parameter from the measured sensor spectral parameters and/or to quantative information about the level of at least one environmental parameter from the measured sensor spectral parameters. The term "principal components analysis (PCA)" refers to a mathematical procedure that is used to reduce multidimensional data sets to lower dimensions for analysis. Principal component analysis is a part of eigenanalysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "spectral parameters" is used to refer to measurable variables of the sensor response. The sensor response is the impedance spectrum of the resonance sensor circuit of the LCR or RFID sensor. In addition to measuring the impedance spectrum in the form of Z-parameters, S-parameters, and other parameters, the impedance spectrum (its both real and imaginary parts) may be analyzed simultaneously using various parameters for analysis, such as, the frequency of the maximum of the real part of the impedance ($F_p$), the magnitude of the real part of the impedance ($Z_p$), the resonant frequency of the imaginary part of the impedance ($F_1$), and the anti-resonant frequency of the imaginary part of the impedance ($F_2$), signal magnitude ($Z_1$) at the resonant frequency of the imaginary part of the impedance ($F_1$), signal magnitude ($Z_2$) at the anti-resonant frequency of the imaginary part of the impedance ($F_2$), and zero-reactance frequency ($F_z$, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra, are called here "features" or "descriptors." The appropriate selection of features is performed from all potential features that can be calculated from spectra. Multivariable spectral parameters are described in U.S. patent application Ser. No. 12/118,950 entitled "Methods and systems for calibration of RFID sensors," which is incorporated herein by reference.

The term "resonance impedance" or "impedance" refers to measured sensor frequency response around the resonance of the sensor from which the sensor "spectral parameters" are extracted.

The term "protecting material" includes, but is not limited to, materials on the LCR or RFID sensor that protect the sensor from an unintended mechanical, physical or chemical effect while still permitting the anticipated measurements to be performed. For example, an anticipated measurement may include solution conductivity measurement wherein a protecting film separates the sensor from the liquid solution yet allows an electromagnetic field to penetrate into solution. An example of a protecting material is a paper film that is applied on top of the sensor to protect the sensor from mechanical damage and abrasion. Another non-limiting example of a protecting material is a polymer film that is applied on top of the sensor to protect the sensor from corrosion when placed in a liquid for measurements. A protecting material may also be a polymer film that is applied on top of the sensor for protection from shortening of the sensor's antenna circuit when placed in a conducting liquid for measurements. Non-limiting examples of protecting films are paper, polymeric, and inorganic films such as polyesters, polypropylene, polyethylene, polyethers, polycarbonate, polyethylene terepthalate, zeolites, metal-organic frameworks, and cavitands. The protecting material can be arranged between the transducer and sensing film to protect the transducer. The protecting material can be arranged on top of the sensing film which is itself is on top of the transducer to protect the sensing film and transducer. The protecting material on top of the sensing film which is itself is on top of the transducer can serve to as a filter material to protect the sensing film from exposure to gaseous or ionic interferences. Non-limiting examples of filter materials include zeolites, metal-organic frameworks, and cavitands.

As used herein the term "sensing materials and sensing films" includes, but is not limited to, materials deposited onto a transducer's electronics module, such as LCR circuit components or an RFID tag, to perform the function of predictably and reproducibly affecting the impedance sensor response upon interaction with the environment. In order to prevent the material in the sensor film from leaching into the liquid environment, the sensing materials are attached to the sensor surface using standard techniques, such as covalent bonding, electrostatic bonding, and other standard techniques known to those of ordinary skill in the art.

The terms "transducer and sensor" are used to refer to electronic devices such as RFID devices intended for sensing. "Transducer" is a device before it is coated with a sensing or protecting film or before it is calibrated for a sensing application. "Sensor" is a device typically after it is coated with a sensing or protecting film and after being calibrated for the sensing application.

As used herein the term "RFID tag" refers to an identification and reporting technology that uses electronic tags for identifying and/or tracking articles to which the RFID tag may be attached. An RFID tag typically includes at least two components where the first component is an integrated circuit (IC) memory chip for storing and processing information and modulating and demodulating a radio frequency signal. This memory chip can also be used for other specialized functions, for example, it can contain a capacitor. It can also contain at least one input for an analog signal such as resistance input, capacitance input, or inductance input. In the case of a chipless RFID tag, the RFID tag may not include an IC memory chip. This type of RFID tag may be useful in applications where a specific RFID tag does not need to be identified, but rather a signal merely indicating the presence of the tag provides useful information (e.g., product security applications). The second component of the RFID tag is an antenna for receiving and transmitting the radio frequency signal.

The term "RFID sensor" is an RFID tag with an added sensing function as, for example, when an antenna of the RFID tag also performs sensing functions by changing its impedance parameters as a function of environmental changes. The accurate determinations of environmental changes with such RFID sensors are performed by analysis of resonance impedance. For example, RFID tags may be converted into RFID sensors by coating the RFID tag with a sensing film. By coating the RFID tag with a sensing film, the electrical response of the film is translated into simultaneous changes to the impedance response, resonance peak position, peak width, peak height and peak symmetry of the impedance response of the sensor antenna, magnitude of the real part of the impedance, resonant frequency of the imaginary part of the impedance, anti-resonant frequency of the imaginary part of the impedance, zero-reactance frequency, phase angle, and magnitude of impedance, and others as described in the definition of the term sensor "spectral parameters." The "RFID sensor" can have an integrated circuit (IC) memory chip attached to the antenna or can have no IC memory chip. An RFID sensor without an IC memory chip is an LCR sensor. An LCR sensor is comprised of known components, such as at least one inductor (L), at least one capacitor (C), and at least one resistor (R) to form an LCR circuit.

The term "single-use container" includes, but is not limited to, manufacturing or monitoring equipment, and packaging, which may be disposed of after use or reconditioned for reuse. Single-use packaging in the food industry includes, but is not limited to, food and drinks packaging, and candy and confection boxes. Single-use monitoring components include, but are not limited to, single-use cartridges, dosimeters, and collectors. Single use manufacturing containers include, but are not limited to, single-use vessels, bags, chambers, tubing, connectors, and columns.

The term "writer/reader" includes, but is not limited to, a combination of devices to write and read data into the memory of the memory chip and to read impedance of the antenna. Another term for "writer/reader" is "interrogator."

In accordance with embodiments disclosed herein, an LCR or an RFID sensor for sensing vapors, vapor mixtures, and biological species is described. As previously described, the RFID sensor includes an RFID tag coated with the coordination compound of a primary alkyl amine and a metal nanoparticle. In one embodiment, a passive RFID tag may be employed. As will be appreciated, an RFID tag may include an IC memory chip, which is connected to an antenna coil for communication with a writer/reader. The IC memory chip can be read by illuminating the tag by a radio frequency (RF) and/or microwave carrier signal sent by the writer/reader. When the RF and/or microwave field passes through the antenna coil, an AC voltage is generated across the coil. The voltage is rectified in the microchip to result in a DC voltage for the microchip operation. The IC memory chip becomes functional when the DC voltage reaches a predetermined level. By detecting the RF and/or microwave signal backscattered from the microchip, the information stored in the microchip can be fully identified. The distance between the RFID tag/sensor and the writer/reader is governed by the design parameters that include operating frequency, RF and/or microwave power level, the receiving sensitivity of the reader/writer, antenna dimensions, data rate, communication protocol, and microchip power requirements. The distance between the "RFID sensor" without an IC memory chip (chipless RFID sensor or LCR sensor or LCR transducer) and the sensor reader is governed by the design parameters that include operating frequency, RF or microwave power level, the receiving sensitivity of the sensor reader, and antenna dimensions.

In one embodiment a passive RFID tag with or without an IC memory chip may be employed. Advantageously, a passive RFID tag does not rely on a battery for operation. However, the communication distance between the writer/reader and RFID tag is typically limited within a proximity distance because the passive tag operates with only microwatts of RF power from the writer/reader. For passive tags operating at 13.56 MHz, the read distance is typically not more than several centimeters. The typical frequency range of operation of 13.56 MHz passive RFID tags for digital ID writing/reading is from 13.553 to 13.567 MHz. The typical frequency range of operation of 13.56-MHz passive RFID sensors for sensing of environmental changes around the RFID sensor is from about 5 MHz to about 20 MHz, more preferably from 10 to 15 MHz. The requirement for this frequency range is to be able to recognize the tag with a writer/reader that operates at 13.56 MHz while the sensor portion of the RFID tag operates from 5 to 20 MHz.

Depositing sensing films onto passive RFID tags creates RFID chemical or biological sensors. RFID sensing is performed by measuring changes in the RFID sensor's impedance as a function of environmental changes around the sensor, as described further below. If the frequency response of the antenna coil, after deposition of the sensing film, does not exceed the frequency range of operation of the tag, the information stored in the microchip can be identified with a conventional RFID writer/reader. An impedance or network analyzer (sensor reader) can read the impedance of the antenna coil to correlate the changes in impedance to the chemical and biological species of interest and to physical, chemical, or/and biological changes of environmental parameters around the sensor.

In operation, after coating of the RFID tag with a chemically sensitive film, both the digital tag ID and the impedance of the tag antenna may be measured. The measured digital ID provides information about the identity of the tag itself, such as an object onto which this tag is attached, and the properties of the sensor (e.g. calibration curves for different conditions, manufacturing parameters, expiration date, etc.). For multi-component detection, multiple properties from the measured real and imaginary portions of the impedance of a single RFID sensor may be determined, as described further below.

In summary, and in accordance with the embodiments described herein, in order to achieve high selectivity detection of analytes in the presence of high levels of interferences, the sensor should exhibit a number of characteristics. First, the selected transducer should include a multivariate output to independently detect the effects of different environmental parameters on the sensor. Second, the sensing material should have a preserved magnitude of response to an analyte over a wide concentration range of an interferent. The response to the relatively small analyte concentrations should not be fully suppressed by the presence of the relatively high concentrations of the interferents. Third, the response of the sensing material to interference species is allowed and may exist but should not compete with the response to the analyte and should be in a different direction of the multivariate output response of the transducer.

To achieve these characteristics, in one embodiment, the sensing material has multiple response mechanisms to vapors where these response mechanisms are related to the changes of dielectric constant, resistance, and swelling of the sensing material where these changes are not fully correlated with each other and produce different patterns upon exposure to individual vapors and their mixtures. Further, the LCR transducer can have multiple components of LCR response from the LCR circuit where these multiple components of LCR response originate from the different factors affecting the transducer circuit with the non-limiting examples that include material resistance and capacitance, contact resistance and capacitance between the transducer and sensing material, and resistance and capacitance between the transducer substrate and sensing material. Further, the LCR transducer can have multiple conditions of LCR circuit operation where an integrated circuit chip is a part of the sensor circuit.

Thus, one method for controlling the selectivity of the sensor response involves powering of the integrated circuit chip to affect the impedance spectral profile. The different impedance spectral profiles change the selectivity of sensor response upon interactions with different vapors. The IC chip or IC memory chip on the resonant antenna contains a rectifier diode and it can be powered at different power levels to influence the impedance spectral profile of the sensor. The differences in spectral profiles at different power levels are pronounced in different values of $F_p$, $F_1$, $F_2$, $F_z$, $Z_p$, $Z_1$, $Z_2$, and calculated values of C and R. In one embodiment, the enhanced sensor selectivity is achieved through the appropriate selection of at least one power level of the IC chip or IC memory chip operation. In another embodiment, the enhanced sensor selectivity is achieved through the appropriate selection of at least two power levels of the IC chip or IC memory chip operation and analyzing the combined impedance spectral profiles of the sensor under different power levels. Powering of the sensor with at least two power levels is performed in the alternating fashion between a relatively low and relatively high power. The alternating powering of the sensor with at least two power levels is performed on the time scale that is at least 5 times faster than the dynamic changes in the measured environmental parameters. In all these embodiments, powering at different power levels is in the range from −50 dBm to +40 dBm and provides the ability to detect more selectively more analytes and/or to reject more selectively more interferences.

Another method of controlling the selectivity of the sensor response involves applying different powers to the LCR or to RFID sensor to affect the dipole moment, the dielectric constant, and/or temperature of the material in proximity to the sensor. The material in proximity to the sensor refers to the sensing material deposited onto the sensor and/or the fluid under investigation. These changes in the dipole moment, the dielectric constant, and/or temperature of the material in proximity to the sensor when exposed to different power levels of LCR or RFID sensor operation originate from the interactions of the electromagnetic field with these materials. Powering of the sensor with at least two power levels is performed in the alternating fashion between a relatively low and relatively high power. The alternating powering of the sensor with at least two power levels is performed on the time scale that is at least 5 times faster than the dynamic changes in the measured environmental parameters. In all these embodiments, powering at different power levels is in the range from −50 dBm to +40 dBm and provides the ability to detect more selectively more analytes and/or to reject more selectively more interferences.

Figure 2:
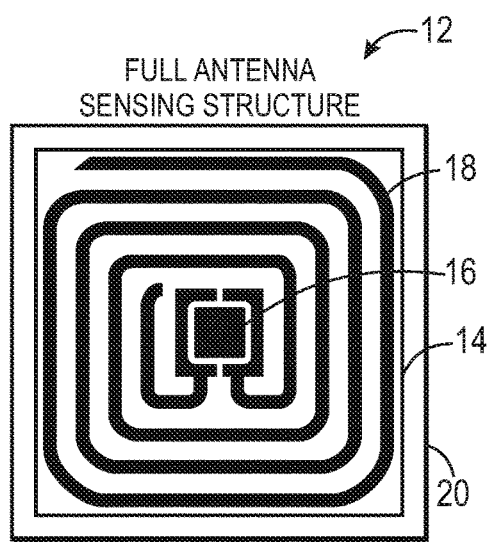
FIG. 2 illustrates an RFID sensor, in accordance with embodiments of the invention.

Turning now to the figures and referring initially to FIG. 1, a sensing system 10 is provided to illustrate the principle of selective vapor sensing utilizing an RFID sensor 12 having a sensing material 14, namely the coordination compound of a primary alkyl amine and a metal nanoparticle, coated thereon. Referring briefly to FIG. 2, the sensor 12 is a resonant circuit that includes an inductor-capacitor-resistor structure (LCR) coated with the sensing material 14. The sensing material 14 is applied onto the sensing region between the electrodes, which form sensor antenna 18 that constitute the resonant circuit. As will be described further below, by applying the sensing material 14 onto the resonant circuit, the impedance response of the circuit will be altered. The sensor 12 may be a wired sensor or a wireless sensor. The sensor 12 may also include a memory chip 16 coupled to resonant antenna 18 that is coupled to a substrate 20. The memory chip 16 may include manufacturing, user, calibration and/or other data stored thereon. The memory chip 16 is an integrated circuit device and it includes RF signal modulation circuitry fabricated using a complementary metal-oxide semiconductor (CMOS) process and a nonvolatile memory. The RF signal modulation circuitry components include a diode rectifier, a power supply voltage control, a modulator, a demodulator, a clock generator, and other components.

Figure 3:
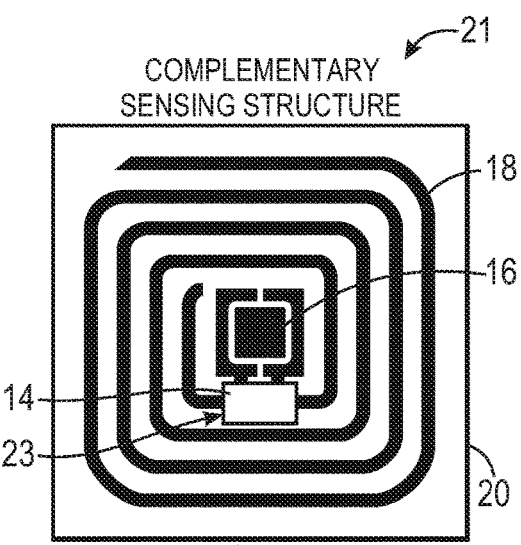
FIG. 3 illustrates an RFID sensor, in accordance with alternate embodiments of the invention.

FIG. 3 illustrates an alternative embodiment of the sensor 12, designated by reference numeral 21, wherein a complementary sensor 23 comprising the sensing material 14 is attached across the antenna 18 and the integrated circuit (IC) memory chip 16 to alter the sensor impedance response. In another embodiment (not illustrated), a complementary sensor may be attached across an antenna that does not have an IC memory chip and alters sensor impedance response. Non-limiting examples of complementary sensors are interdigitated sensors, resistive sensors, and capacitive sensors. Complementary sensors are described in U.S. patent application Ser. No. 12/118,950 entitled "Methods and systems for calibration of RFID sensors," which is incorporated herein by reference.

In one embodiment, a 13.56 MHz RFID tag may be employed. During operation of the sensing system 10, the impedance Z(f) of the sensor antenna 18 and the digital sensor calibration parameters stored on the memory chip 16 may be acquired. Referring again to FIG. 1, measurement of the resonance impedance Z(f) of the antenna 18 and the reading/writing of digital data from the memory chip 16 are performed via mutual inductance coupling between the RFID sensor antenna 18 and the pickup coil 22 of a reader 24. As illustrated, the reader 24 may include an RFID sensor impedance reader 26 and an integrated circuit memory chip reader 28. The interaction between the RFID sensor 12 and the pickup coil 22 can be described using a general mutual inductance coupling circuit model. The model includes an intrinsic impedance $Z_C$ of the pickup coil 22 and an intrinsic impedance $Z_S$ of the sensor 12. The mutual inductance coupling B and the intrinsic impedances $Z_C$ and $Z_S$ are related through the total measured impedance $Z_T$ across the terminal of the pickup coil 22, as represented by the following equation:

$$Z_T = Z_C + (\omega^2 B^2 / Z_S), \quad (1)$$

wherein ω is the radian carrier frequency and B is the mutual inductance coupling B coefficient.

Sensing is performed via monitoring of the changes in the properties of the sensing material 14 as probed by the electromagnetic field generated in the antenna 18 (FIG. 2). Upon reading the RFID sensor 12 with the pickup coil 22, the electromagnetic field generated in the sensor antenna 18 extends out from the plane of the sensor 12 and is affected by the dielectric property of an ambient environment providing the opportunity for measurements of physical, chemical, and biological parameters.

Similarly, sensing is performed via monitoring of the changes in the properties of the sensing material 14 as probed by the electromagnetic field generated in the complementary sensor 23 (FIG. 3). Upon reading the RFID sensor 12 with the pickup coil 22, the electromagnetic field generated in the complementary sensor 23 extends out from the plane of the complementary sensor 23 and is affected by the dielectric property of an ambient environment providing the opportunity for measurements of physical, chemical, and biological parameters.

Figure 4:
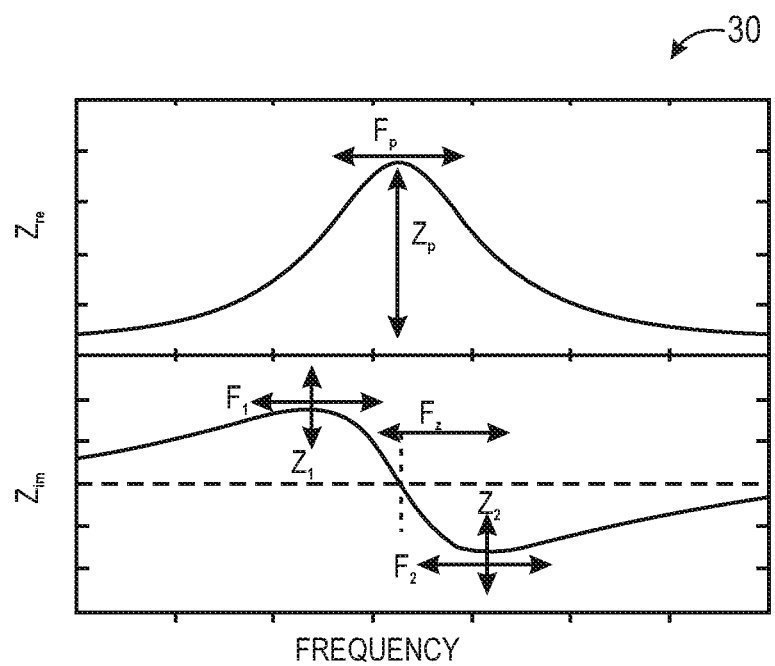
FIG. 4 illustrates measured responses of an RFID sensor, in accordance with embodiments of the invention.

FIG. 4 illustrates an example of measured responses of an exemplary RFID sensor 12, in accordance with embodiments of the invention, which includes the sensor's full impedance spectra and several individually measured spectral parameters. To selectively detect several vapors or fluids using a single RFID sensor, such as the RFID sensor 12, the real $Z_{re}(f)$ and imaginary $Z_{im}(f)$ parts of the impedance spectra $Z(f)=Z_{re}(f)+jZ_{im}(f)$ are measured from the sensor antenna 18 coated with a sensing material and at least four spectral parameters are calculated from the measured $Z_{re}(f)$ and $Z_{im}(f)$, as illustrated in the plot 30 of FIG. 4. Seven spectral parameters can be calculated as illustrated in the plot 30 of FIG. 4. These parameters include the frequency position $F_p$ and magnitude $Z_p$ of $Z_{re}(f)$, the resonant $F_1$ and anti-resonant $F_2$ frequencies of $Z_{im}(f)$, the impedance magnitudes $Z_1$ and $Z_2$ at $F_1$ and $F_2$ frequencies, respectively, and the zero-reactance frequency $F_Z$. Additional parameters, such as quality factor may also be calculated. From the measured parameters, resistance R, capacitance C, and other parameters of the sensing film-coated resonant antenna 18 can be also determined. Multivariate analysis may be used to reduce the dimensionality of the impedance response, either from the measured real $Z_{re}(f)$ and imaginary $Z_{im}(f)$ parts of the impedance spectra or from the calculated parameters $F_p$, $Z_p$, $F_1$ and $F_2$, and possibly other parameters to a single data point in multidimensional space for selective quantization of different vapors or fluids, as will be appreciated by those skilled in the art, and as will be described further below.

The presence of even relatively low levels of interferences (0.1-10 fold overloading levels) represents a significant limitation for individual sensors due to their insufficient selectivity. This problem can be addressed with an introduction of a concept of sensor arrays. Unfortunately, in practical situations (e.g. urban, environmental, and workplace monitoring, breath analysis, and others), sensor arrays suffer from interference effects at high ($10^2$-$10^6$ fold) overloading levels. These interference effects reduce the use of both sensors and sensor arrays. Advantageously, embodiments described herein provide techniques to overcome these two key scientific limitations of existing sensors and sensor arrays, such as difficulty or inability of operating with high overloading from interferences and of selective measurements of multiple vapors and their mixtures using a single sensor.

The well-accepted limitations of impedance spectroscopy in practical sensors for trace analyte detection include relatively low sensitivity and prohibitively long acquisition times over the broad frequency range. Embodiments described herein enhance the ability to measure changes in properties of the sensing material by putting the material onto the electrodes of the resonant LCR sensor circuit. Similarly, the disclosed embodiments enhance the ability to measure changes in properties of the fluid in proximity to the electrodes of the resonant LCR sensor circuit. Experimental testing examined the effects of changing dielectric constant on sensing electrodes both with and without a resonator. Compared to the conventional impedance spectroscopy, the bare resonant LCR sensor provided an at least 100-fold enhancement in the signal-to-noise (SNR) over the smallest measured range of $\Delta\in$ with the corresponding improvement of detection limit of dielectric constant determinations.

Performance of the LCR sensor as analyzed using multivariate analysis tools provides an advantage of improved selectivity over the processing of individual responses of individual sensors. In particular, test results indicate the relations between $F_p$ and $Z_p$ and the relations between calculated sensor resistance R and calculated sensor capacitance C have much less selectivity between responses to different vapors or fluids as compared to the relations between multivariable parameters that show more variation, as discussed in detail below. Further, the LCR sensors demonstrate independent contact resistance and contact capacitance responses that improve the overall selectivity of the multivariable response of the LCR sensors. This selectivity improvement originates from the independent contributions of the contact resistance and contact capacitance responses to the equivalent circuit response of the sensor.

Diverse sensing materials may be advantageously utilized on the sensing region of the LCR resonant sensor because analyte-induced changes in the sensing material film affect the impedance of the antenna LCR circuit through the changes in material resistance and capacitance, contact resistance and capacitance between the transducer and sensing material, and resistance and capacitance between the transducer substrate and sensing material. Such changes provide diversity in response of an individual RFID sensor and provide the opportunity to replace a whole array of conventional sensors with a single LCR or RFID sensor.

Figure 5:
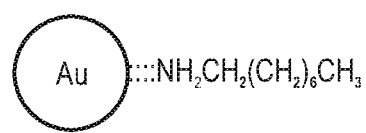
FIG. 5 illustrates a sensing material, in accordance with embodiments of the invention.

Sensing films for the disclosed LCR and RFID sensors may include a variety of coordination compounds of a primary alkyl amine, trialkylphosphine, trialkylphosphine oxide, alkyldithiocarbamate, alkylxanthate or any combination thereof and a metal nanoparticle, as long as the environmental changes are detectable by changes in resonant LCR circuit parameters. The primary alkyl amine, trialkylphosphine, trialkylphosphine oxide, alkyldithiocarbamate, alkylxanthate, or combinations thereof may also be referred to as a ligand or a combination of ligands, which binds to a central metal atom to form a coordination complex. The exemplary coordination compound may be represented by the formula: $(X)_n$-M where X includes an alkylamine group having the formula ($R-NH_2$), an alkylphosphine having the formula ($R_3-P$), an alkylphosphine oxide having the formula ($R_3P=O$), an alkyldithiocarbamate having the formula ($R_2NCS_2$), an alkylxanthate having the formula ($ROCS_2$), or any combination thereof and M is the metal nanoparticle. The value of n may be 1, 2, 3, or greater. The alkyl group R may be represented by the formula: $C_yH_{2y+1}$, where y=1 to 18. Metals that may be used for the metal nanoparticle M include, but are not limited to, gold, silver, platinum, palladium, alloys thereof, other highly conductive metal nanoparticles, or combinations thereof. In certain embodiments, a weak covalent bond exists between the metal nanoparticle and the ligand. In one embodiment, the coordination compound is formed between an octylamine-capped C8 ligand and a gold nanoparticle, as shown in FIG. 5. Other embodiments may utilize other coordination compounds of a primary alkyl amine, trialkylphosphine, trialkylphosphine oxide, alkyldithiocarbamate, or alkylxanthate, and the metal nanoparticle.

Non-limiting examples of sensing materials include octylamine-capped C8 ligand and a gold nanoparticle, octylamine-capped C8 ligand and a silver nanoparticle, octylamine-capped C8 ligand and a platinum nanoparticle, octylamine-capped C8 ligand and a palladium nanoparticle, nonylamine-capped C8 ligand and a gold nanoparticle, and heptylamine-capped C8 ligand and a gold nanoparticle. The use of these materials provides the ability to tailor the relative direction of sensing response upon exposure to vapors of different natures. The different partition coefficients of vapors into these or other sensing materials further modulate the diversity and relative direction of the response.

"Composites" are materials made from two or more constituent materials with significantly different physical or chemical properties, which remain separate and distinct on a macroscopic level within the finished structure. Non-limiting examples of composites include carbon black composites with the various coordination compounds of a primary alkyl amine and a metal nanoparticle discussed in detail above. "Nanocomposites" are materials made from two or more constituent materials with significantly different physical or chemical properties, which remain separate and distinct on a nanoscale level within the finished structure. Non-limiting examples of nanocomposites include: carbon nanotube nanocomposites with exemplary coordination compounds; semiconducting nanocrystal quantum dot nanocomposites with exemplary coordination compounds, metal oxide nanowires, and carbon nanotubes; metal nanoparticles or nanoclusters functionalized with carbon nanotubes.

Sensing materials exhibit analyte responses, which can be described by one or more of three response mechanisms of LCR or RFID sensors, such as resistance changes, dielectric constant changes, and swelling changes. A composite sensing material can be constructed which incorporates the exemplary coordination compounds with multiple different individual sensing materials, which each respond to analytes by predominantly different response mechanisms. Such composite sensing materials produce an enhanced diversity in the multivariate response. Such composite sensing materials may be homogeneously or inhomogeneously mixed or locally patterned over specific portions of the LCR resonator.

For example, a wide range of metal oxide semiconductor materials (e.g. ZnO, $TiO_2$, $SrTiO_3$, $LaFeO_3$, etc) exhibit changes in resistance upon exposure to analyte gases, but some mixed metal oxides (e.g. CuO—$BaTiO_3$, ZnO—$WO_3$) change their permittivity/capacitance upon exposure to analyte vapors. By combining these materials either as mixtures, or by spatially separated deposition onto the same sensor, their separate contributions to the local environment surrounding the sensor are used to enhance the diversity of response mechanisms for a single analyte, thus enhancing selectivity.

As a further example, the coordination compounds of a primary alkyl amine and a metal nanoparticle are used as vapor sensing materials because of their strong changes in resistance due to localized swelling induced by analyte adsorption into the ligand shell and the subsequent change in tunneling efficiency between neighboring conducting nanoparticles and dielectric constant changes of the environment between these conducting nanoparticles. In combination with a dielectric polymer (non-limiting examples include silicones, poly(etherurethane), polyisobutylene siloxane fluoroalcohol, etc.), conjugated polymer (polyaniline, polythiophene, poly(vinyl ferrocene), poly(fluorene)-diphenylpropane), poly(3,4-ethylenedioxythiophene) polypyrrole, bilypyrrole) or any other material (non-limiting examples include porphyrins, metalloporphyrins, metallophthalocyanines, carbon nanotubes, semiconducting nanocrystals, metal oxide nanowires) that responds to analyte adsorption with more pronounced changes in capacitance or resistance, a sensor with a wider range of analyte responses is developed. Other examples of materials that may be combined with the exemplary coordination compounds are described in U.S. patent application Ser. No. 12/942,732 entitled "Highly Selective Chemical and Biological Sensors," which is incorporated herein by reference.

Further, in order to avoid potentially deleterious effects of disparate materials on each other in a composite sensing material (e.g. high dielectric constant medium suppressing conduction in a conductive filler material), the material components are chosen to locally phase separate due to hydrophylic/hydrophobic interactions or mutual immiscibility, allowing the different mechanisms active in each component to be sensed by the sensor. In another embodiment, a composite sensing material can be formed as sectors of individual materials deposited adjacent to each other onto a single sensor. In another embodiment, a composite sensing material can be formed as layers of individual materials deposited on top of each other onto a single sensor.

To further improve selectivity of response, overcoating of sensing films with auxiliary membrane filter films may be performed. Non-limiting examples of these filter films include zeolite, metal-organic framework, and cavitand filters.

These diverse sensing materials shown as non-limiting examples are provided on the sensing region of the LCR or RFID resonant sensor because analyte-induced changes in the sensing material film affect the impedance of the antenna LCR circuit through the changes in material resistance and capacitance, contact resistance and capacitance between the transducer and sensing material, resistance and capacitance between the transducer substrate and sensing material. Such changes provide diversity in response of an individual RFID sensor and provide the opportunity to replace a whole array of conventional sensors with a single LCR or RFID sensor, as illustrated further below, with regard to EXPERIMENTAL DATA.

Experimental Data

Resonant antenna structures, such as those described above, were used for demonstration of the disclosed techniques. Various sensing materials were applied onto the resonant antennas by conventional draw-coating, drop coating, and spraying processes. Measurements of the impedance of the RFID sensors were performed for example with a network analyzer (Model E5062A, Agilent Technologies, Inc., Santa Clara, Calif.) under computer control using LabVIEW. The network analyzer was used to scan the frequencies over the range of interest (i.e., the resonant frequency range of the LCR circuit) and to collect the impedance response from the RFID sensors.

For gas sensing, different concentrations of vapors were generated using an in-house built computer-controlled vapor-generation system. Collected impedance data was analyzed using KaleidaGraph (Synergy Software, Reading, Pa.) and PLS_Toolbox (Eigenvector Research, Inc., Manson, Wash.) operated with Matlab (The Mathworks Inc., Natick, Mass.).

EXAMPLE

Selective Detection Of Individual Nine Alcohols With A Single Sensor

Figure 6:
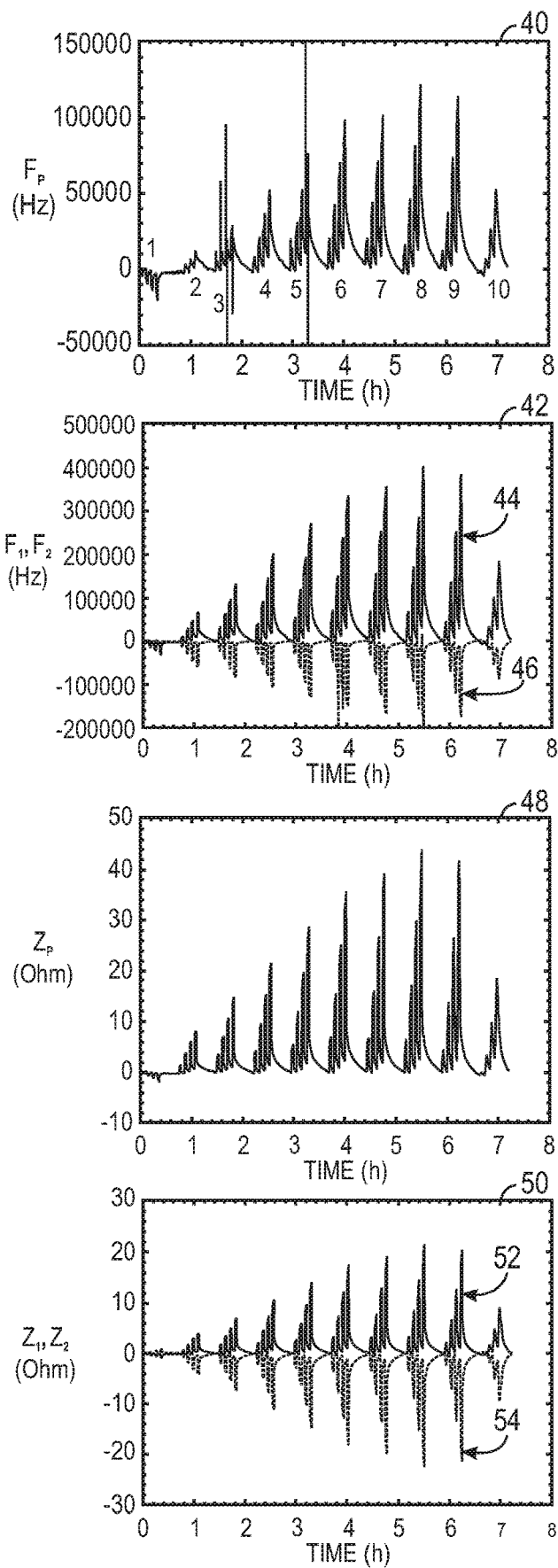
FIGS. 6 and 7 illustrate test data demonstrating a single sensor capable of discriminating between water vapor and nine individual alcohol vapors from their homologous series, in accordance with embodiments of the invention.
Figure 7:
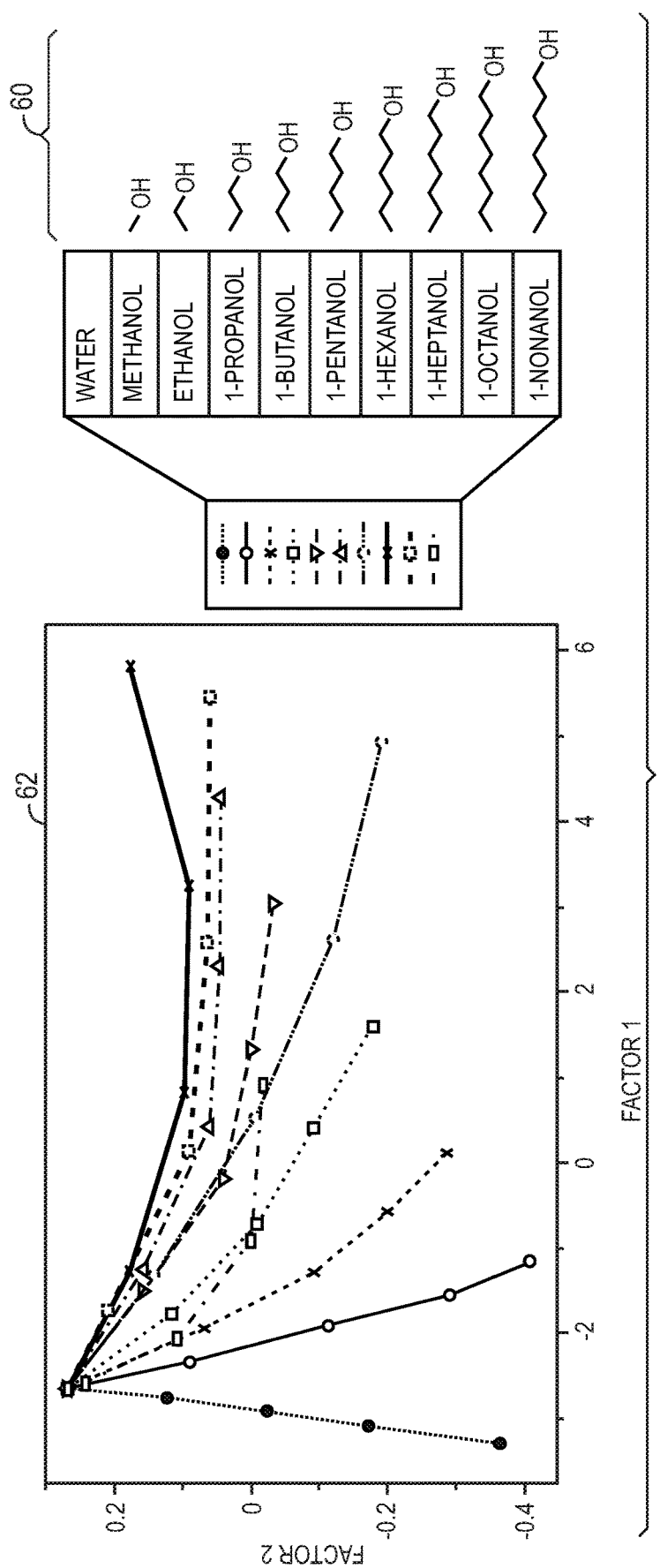

As illustrated in FIGS. 6 and 7, test results were obtained to demonstrate the selective detection of individual, closely related vapors, such as alcohols from their homologous series and water vapor as an interferent, using a single sensor, such as the sensor 12 described above. As illustrated in FIG. 6, the sensor was exposed to the following 10 vapors over a period of time:

| | |
|---|---|
| 1 | water |
| 2 | methanol |
| 3 | ethanol |
| 4 | 1-propanol |
| 5 | 1-butanol |
| 6 | 1-pentanol |
| 7 | 1-hexanol |
| 8 | 1-heptanol |
| 9 | 1-octanol |
| 10 | 1-nonanol |

The structures of the alcohols 60 are illustrated in FIG. 7.

The sensing material used to coat the RFID tag was carefully chosen and provided the ability to selectively detect the listed vapors. In the present experiment, the chosen sensing material was octylamine-capped C8 ligand attached to gold nanoparticles, which was applied as a sensing film onto an RFID sensor chip by drop casting. Specifically, the nanoparticles of the sensing material were synthesized as follows. A solution of $HAuCl_4 3H_2O$ (112 mg) was dissolved in 25 mL of water. While vigorously stirring the solution, oleylamine (830 mg) dissolved in 25 mL of toluene was added and the mixture was stirred until most or all of the Au ions were transferred into the organic layer. After approximately 30 minutes, $NaBH_4$ (0.165 g) in 25 mL of water was added drop-wise and the reaction mixture was stirred for approximately 2 to 3 hours. The reaction mixture was phase separated and the toluene layer dried over anhydrous $MgSO_4$. The toluene layer was reduced to a volume of 5 mL on a rotary evaporator. After addition of ethanol (100 mL) to the toluene layer, the reaction mixture was left at approximately −40 degrees Celsius overnight in a freezer for the nanoparticles to precipitate out. The nanoparticles were separated from the solution by filtering through filter paper (Whatman, Piscataway, N.J.) and later redispersed in approximately 10 mL of toluene.

An interdigital chip served as a complementary sensor that was attached across an antenna of a passive RFID tag. The chip was approximately 2 mm by 2 mm and had gold electrodes that were approximately 10 μm wide and spaced approximately 10 μm from each other. During the experiment, the RFID sensor was incrementally exposed to 10 vapors over a period of time. The test was conducted in steps, where the concentration of each respective vapor was increased with each step. Measurements were performed with concentrations of all vapors at 0, 0.089, 0.178, 0.267, and 0.356 $P/P_o$, where P is the partial pressure and $P_o$ is the saturated vapor pressure. By monitoring changes in certain properties and examining various responses over time and at increasing concentration levels, the data demonstrated the ability to distinguish the 10 vapors tested in the above-described experiment.

For instance, the frequency position $F_p$, the resonant $F_1$ and anti-resonant $F_2$ frequencies of $Z_{im}(f)$, the magnitude $Z_p$ of the real part of the total resistance $Z_{re}(f)$, and the impedance magnitudes $Z_1$ and $Z_2$ at $F_1$ and $F_2$ frequencies, respectively, are illustrated in FIG. 6, as response plots 40, 42, 48, and 50, respectively. The tests for each vapor were conducted and plotted over 4 increments of increasing concentration, as clearly indicated by the stepped nature of the response for each vapor. The relative differences in the direction and the magnitude of these responses constitute a robust response pattern for these vapors and their different concentrations using a single sensor. For example, referring to the plot 40 of the frequency position $F_p$, the frequency position $F_p$ for each vapor (1-10) exhibits four steps, correlative to the increases in concentration of each vapor over time. From examining this plot alone, certain of the vapors can clearly be distinguished from one another. By way of example, the frequency position $F_p$ response for 1-heptanol (8) is very strong, and notably discernable from each of the other responses. Accordingly, the exemplary RFID sensor is able to selectively detect 1-heptanol (8). In contrast, when viewing the frequency position $F_p$ response of 1-pentanol (6), it appears very similar to the frequency position $F_p$ of 1-hexanol (7). Based solely on the frequency position $F_p$ response, the exemplary RFID sensor may not be suitable for detecting and distinguishing between these two vapors.

However, as previously described, a number of other responses may also be analyzed and may provide further information that may be manipulated and analyzed in order to provide a way to distinguish vapors, wherein one particular response may not be sufficient. Referring to the test data for the magnitude $Z_p$ response plot 48, the magnitude $Z_p$ of 1-pentanol (6) is distinguishable from the magnitude $Z_p$ of 1-hexanol (7). Accordingly, the exemplary RFID sensor may be sufficient for distinguishing such vapors, when other responses, such as the magnitude $Z_p$ (as opposed to the frequency position $F_p$ response alone), are analyzed.

One convenient way of analyzing various responses of the sensor is to use principal components analysis (PCA) to produce a multivariate signature. As will be appreciated, PCA analysis is a mathematical process, known to those skilled in the art, that is used to reduce multidimensional data sets to lower dimensions for analysis. For instance, the various responses for each vapor at a given concentration may be reduced to a single data point, and from this, a single response for each vapor, which may be represented as a vector, may be discerned, as illustrated in FIG. 7. FIG. 7 represents a PCA plot 62 of the various responses of the 10 vapors described with reference to FIG. 6. As will be appreciated, FACTOR1 represents the response with the most variation, while FACTOR2 represents the response with the next most variation. As shown in FIG. 7, the ten vapors are clearly distinguishable from one another. Accordingly, the instant test data provides support for a sensor capable of discerning between at least ten vapors, here water (1), methanol (2), ethanol (3), 1-propanol (4), 1-butanol (5), 1-pentanol (6), 1-hexanol (7), 1-heptanol (8), 1-octanol (9), and 1-nonanol (10). Individual sensors may not achieve this level of vapor discrimination, while this discrimination was achieved in the Example with a single sensor.

In addition, vapor mixtures may also be discernable from the PCA plot. For instance, one may be able to extrapolate a vector plot of a mixture of methanol (2) and 1-octanol (9). Such additional extrapolated data may also be used to selectively detect mixtures of selected vapors. Further, by varying the selected sensing material, even greater numbers of selective vapor detection has been demonstrated, utilizing a single RFID sensor.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of detecting chemical or biological species in a fluid, comprising:
   measuring a real part and an imaginary part of an impedance spectrum of a resonant sensor antenna coated with a coordination compound of a ligand and a metal nanoparticle, wherein the ligand comprises a primary alkyl amine, trialkylphosphine, trialkylphosphine oxide, alkyldithiocarbamate, alkylxanthate or any combination thereof;
   calculating at least six spectral parameters of the resonant sensor antenna coated with the coordination compound, wherein the at least six spectral parameters comprise at least six of a frequency of a maximum of the real part of the impedance spectrum, a magnitude of the real part of the impedance spectrum, a resonant frequency of the imaginary part of the impedance spectrum, an anti-resonant frequency of the imaginary part of the impedance spectrum, a signal magnitude at the resonant frequency of the imaginary of the impedance spectrum, a signal magnitude at the anti-resonant frequency of the imaginary part of the impedance spectrum, and a zero-reactance frequency of the imaginary portion of the impedance spectrum;

reducing the impedance spectrum to a single data point using multivariate analysis to selectively identify an analyte; and determining one or more environmental parameters from the impedance spectrum.

2. The method, as set forth in claim 1, wherein the coordination compound has the formula:

$(X)_n$-M, wherein:

X comprises an alkylamine group having the formula (R—$NH_2$), an alkylphosphine having the formula ($R_3$—P), an alkylphosphine oxide having formula ($R_3$P=O), an alkyldithiocarbamate having the formula ($R_2NCS_2$), an alkylxanthate having the formula ($ROCS_2$), or any combination thereof;

R comprises an alkyl group, wherein the alkyl group has the formula $C_yH_{2y+1}$, wherein y=1 to 18;

n is 1, 2, or 3; and

M comprises the metal nanoparticle of gold, silver, platinum, palladium, alloys thereof, highly conductive metal nanoparticles, or any combination thereof.

3. The method, as set forth in claim 1, wherein measuring the impedance spectrum and calculating the at least six spectral parameters comprises measuring over a resonant frequency range of the resonant sensor.

4. The method, as set forth in claim 1, wherein calculating at least six spectral parameters comprises calculating the frequency of the maximum of the real part of the impedance spectrum and the magnitude of the real part of the impedance spectrum.

5. The method, as set forth in claim 1, wherein calculating at least six spectral parameters comprises calculating the resonant frequency of the imaginary part of the impedance spectrum and the anti-resonant frequency of the imaginary part of the impedance spectrum.

6. The method, as set forth in claim 1, wherein determining one or more environmental parameters from the impedance spectrum comprises determining a resistance and a capacitance of the resonant sensor coated with the coordination compound.

7. The method, as set forth in claim 1, wherein reducing the impedance spectrum to a single data point comprises calculating a multivariate signature.

8. The method, as set forth in claim 7, wherein calculating the multivariate signature comprises using principal components analysis.

9. The method, as set forth in claim 1, wherein measuring the impedance spectrum and calculating the at least six spectral parameters comprises supplying power to an integrated circuit (IC) chip of the resonant sensor at a first predetermined power level.

10. The method, as set forth in claim 9, wherein measuring the impedance spectrum and calculating at least six spectral parameters comprises alternating the power supplied to the IC chip of the resonant sensor between the first predetermined power level and a second predetermined power level.

11. The method, as set forth in claim 10, wherein the first predetermined power level and the second predetermined power level are between −50 dBm and +40 dBm.

* * * * *